United States Patent [19]

Bernard et al.

[11] Patent Number: 5,607,921
[45] Date of Patent: Mar. 4, 1997

[54] STABILIZED COSMETIC OR DERMATOLOGICAL COMPOSITION CONTAINING SEVERAL PRECURSORS OF THE SAME ACTIVE AGENT IN ORDER TO MAXIMIZE ITS RELEASE, AND USE THEREOF

[75] Inventors: Dominique Bernard, Paris; Quang Lan Nguyen, Antony, both of France

[73] Assignee: L'Oreal, Paris, France

[21] Appl. No.: 380,977

[22] Filed: Jan. 31, 1995

[30] Foreign Application Priority Data

Jan. 31, 1994 [FR] France .................................. 94 01031

[51] Int. Cl.$^6$ ............. A61K 31/70; A61K 31/59
[52] U.S. Cl. ................ 514/23; 514/25; 514/167; 514/168; 514/725; 514/844; 514/845; 514/846; 514/847; 514/848; 514/970
[58] Field of Search ............... 514/23, 25, 167, 514/168, 725, 844, 845, 846, 847, 848, 970

[56] References Cited

U.S. PATENT DOCUMENTS 5,380,764  1/1995  Herzog .................... 514/725

FOREIGN PATENT DOCUMENTS

| 0371844 | 6/1990 | European Pat. Off. . |
|---|---|---|
| 0487404 | 5/1992 | European Pat. Off. . |
| 0506961 | 10/1992 | European Pat. Off. . |
| 2473887 | 7/1981 | France . |
| 2694692 | 2/1994 | France . |
| 4328871 | 3/1995 | Germany . |
| 61-152613 | 7/1986 | Japan . |
| 01093520 | 4/1989 | Japan . |
| 2266052 | 10/1993 | United Kingdom . |
| WO86/06275 | 11/1986 | WIPO . |
| 9423694 | 1/1993 | WIPO . |

OTHER PUBLICATIONS

Proserpio et al. *Cosmet. Toiletries,* vol. 105(10), pp. 67–70, (1990).*
Proserpio et al. Cosmet. Toiletries, Ed. Ital., vol. 9(3), pp. 29–32 and 34, (1988).*

*Primary Examiner*—Gary E. Hollinden
*Assistant Examiner*—Howard C. Lee
*Attorney, Agent, or Firm*—Oblon, Spivak, McClelland, Maier & Neustadt, P.C.

[57] ABSTRACT

A stabilized composition capable of releasing an active agent in contact with the skin, contains at least two precursors of this same active agent, capable of simultaneously releasing this active agent by at least two different specific enzymatic reactions in order to release a large amount of active agent at a faster rate than the sum of the rates of the first enzymatic reaction and of the second enzymatic reaction taken separately, the first precursor being chosen from active agent monosaccharide derivatives and active agent amides. The composition is useful for dermatological and/or cosmetic treatments applied topically.

28 Claims, 1 Drawing Sheet

STABILIZED COSMETIC OR DERMATOLOGICAL COMPOSITION CONTAINING SEVERAL PRECURSORS OF THE SAME ACTIVE AGENT IN ORDER TO MAXIMIZE ITS RELEASE, AND USE THEREOF

BACKGROUND OF THE INVENTION

1. Field of the Invention

The present invention relates to a stabilized cosmetic or dermatological composition containing several compounds capable of releasing the same active agent or compound in contact with the skin, including the scalp. The active agents to which the invention applies are all the compounds which are usable in the cosmetic and/or dermatological field for which bioconvertible precursors exist. This composition may be applied to the human body and/or face.

As active agents, special mention may be made of vitamins, lipopeptides, lipoamino acids, α- and β-hydroxy acids (lactic, glycolic, glucuronic acid), antioxidants such as flavonoids (for example, quercetin or rutin), catechins, of which the natural extracts of plants such as tea are composed, and hydrating agents such as polyols (glycerol).

2. Discussion of the Background

There is increasing interest in introducing vitamins such as vitamins A, B, C, D, E and F (essential fatty acids), as well as other active agents, into cosmetic and/or dermatological compositions with a view to providing specific treatments against, for example, excessive weight, skin aging, dry skin, skin pigmentation, acne and certain skin diseases (psoriasis) or, alternatively, in order to promote the cicatrization (scar formation) and/or restructuring of the skin.

In particular, the application of a sufficient amount of ascorbic acid or vitamin C to the skin enables the growth of the connective tissue and, in particular, that of collagen to be stimulated. Ascorbic acid also enables the defenses of the cutaneous tissue against harmful external agents such as ultraviolet rays or pollution, or the adverse effects of medicinal products, alcohol or tobacco, to be strengthened.

Moreover, tocopherols, such as vitamin E, are known to possess both antioxidant properties with respect to cell membrane phospholipids and anti-free-radical (AFR) properties (see "Radicaux libres et Vitamine E", that is "Free radicals and vitamin E" by J. B. Chazan and M. Szulc -Cah. Nutr. Diet. 1987 6 XXII-1- pages 66–76).

In addition, vitamin A or retinol, and also hydroxy acids, are known to combat aging. Furthermore, vitamin A is known to effect cicatrization of the skin.

Unfortunately, most of these active agents (vitamins, antioxidants, hydroxy acids, and the like) are unstable in solution and sensitive to external factors, rendering these solutions ineffective and detracting from the desired efficacy.

The article "Stability of ascorbic acid" by Br. Hajratwala, published in "Sciences Pharmaceutiques Revue" pages 281–286, teaches that ascorbic acid possesses properties of instability in an aqueous medium, in an aerobic and anaerobic medium, with a more marked instability in an aerobic medium. This publication includes an illustration of the behavior of ascorbic acid in the presence of changes in the pH of the ascorbic acid-containing solution and changes in light and temperature, and in the presence of compounds such as surfactants, solvents and catalysts, in particular, metal catalysts.

Different means have been envisaged for stabilizing ascorbic acid. Japanese patents JP 89/115,558 and JP 83/129,892 teach the blocking of the reactive site of ascorbic acid, namely the hydroxyl site, by esterification and/or etherification with, for example, phosphated, sulphated and alkylated derivatives, and the use of these derivatives in cosmetic compositions to play the part of vitamin C. Unfortunately, these latter derivatives are much less effective than free vitamin C (without additional groups). Accordingly, the use of a vitamin C precursors has been envisaged.

Thus, European patent EP 487,404 discloses the use of a glucosyl derivative in dermatological compositions, capable of releasing the ascorbic acid when these compositions are brought into contact with the skin.

Moreover, the esterification of an ascorbic acid derivative and of a tocopherol derivative with phosphoric acid (see "Bioconversion of a vitamin to vitamins C and E in skin" by Kakuji Tojo and Aeric Lee published in J. Cosmet. Chem., 38, pages 333–339), and its use in a composition, have been envisaged. However, this diester displays lower efficacy than that of free ascorbic acid with respect to ascorbic acid and with respect to vitamin E, inferior antioxidant activity to that of free vitamin E.

This same problem is also encountered with any type of active agent.

It is also known, from EP-A-506,961, to use several derivatives of the same active agent in a cosmetic composition, but this document does not teach the enzymatic cleavage of these derivatives on the skin according to two different enzymatic mechanisms. Moreover, the efficacy of the combination described, ester and phosphate, is still insufficient.

Thus, a need remains for a cosmetic and/or dermatological composition containing vitamin derivatives or derivatives of any other active agent achieving the same efficacy as the compositions of free vitamins or active agents, as well as good stability of these vitamins or active agents.

SUMMARY OF THE INVENTION

It has now been discovered, surprisingly, that the use in a composition of at least one first precursor for an active agent, and one second precursor for the active agent capable of simultaneously releasing the same active agent by at least one first specific enzymatic reaction and one second, different, specific enzymatic reaction, the first precursor being chosen from active agent monosaccharide derivatives and active agent amides, enables a large amount of active agent to be released on application of the composition to the skin, at a faster rate than the sum of the rates of the first enzymatic reaction and of the second enzymatic reaction taken separately, while effecting stability of the active agent over time.

In other words, this pair of active agent precursors, differing in their nature, releases the active agent when in contact with the skin by reaction with two different specific enzyme systems present naturally in the skin. In effect, in contact with the *Stratum corneum* (superficial layers of the skin), each active agent precursor is hydrolyzed by the action of a specific enzyme in the skin which possesses its own kinetics. The simultaneous action of two or more different enzyme systems on precursors of the same active agent differing in their nature, enables the free active agent to be released more rapidly and in larger amounts, compared with the action of identical or different enzyme systems separated by an interval of time.

This composition gives good results irrespective of the type of skin to which it is applied, its temperature and its moisture content.

DETAILED DESCRIPTION OF THE PREFERRED EMBODIMENTS

Figure 1:
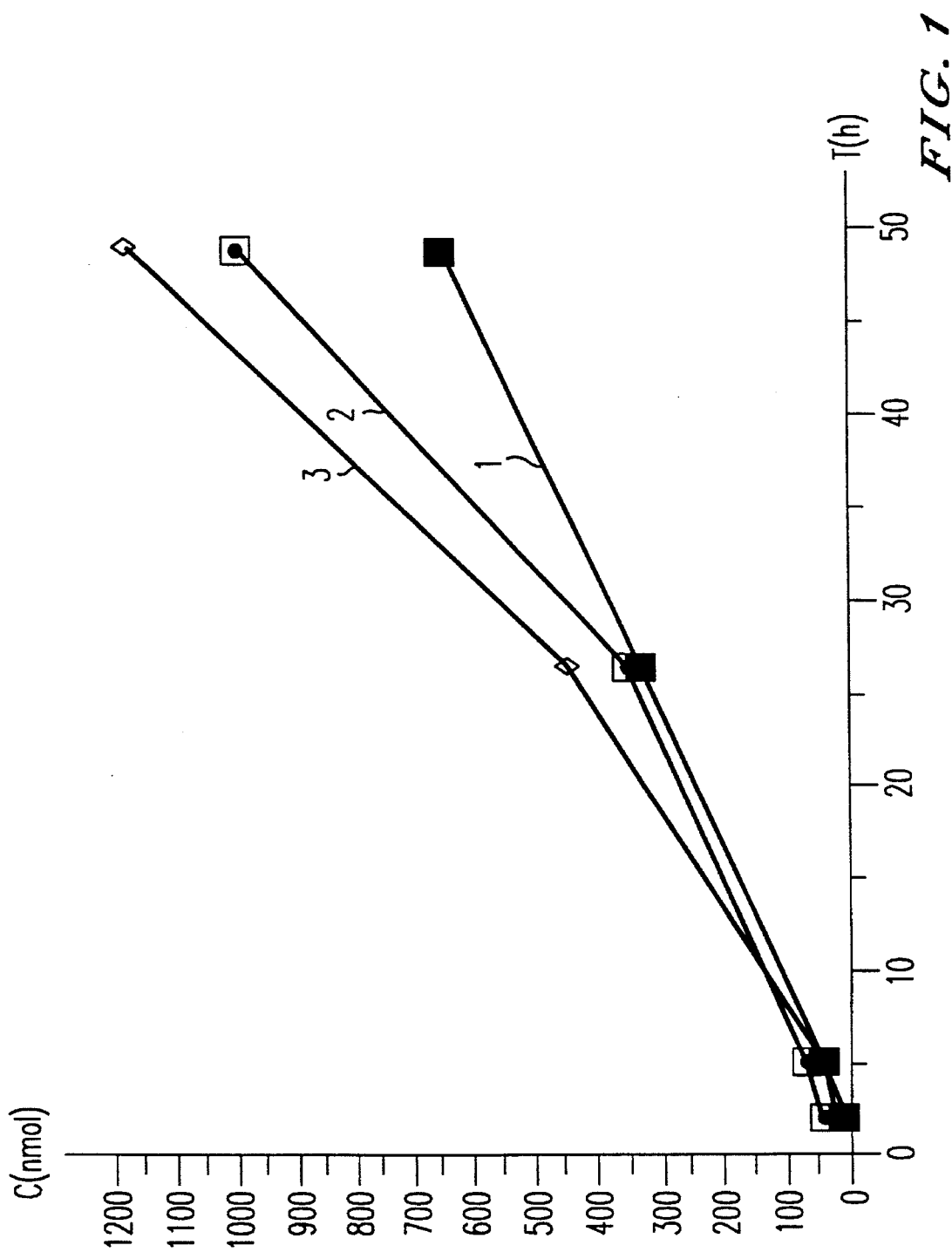
FIG. 1 shows the pattern of release of vitamin C, for different precursors in contact with the Stratum corneum. The ordinate axis represents the amount (C) of vitamin C released in nanomoles and the abscissa axis represents the time (t) in hours.

According to the invention, it is possible to use two or more (a plurality) precursors of the same active agent differing in their nature, optionally combined with one or more (a plurality) other precursors, identical or differing in their nature, of another active agent.

Preferably, the first and second precursors are used in the form of solutions. The pH of the solution containing the precursors is preferably in the vicinity of that of the skin surface, namely a pH of approximately 5.5, in order to avoid any adverse effect on the skin. If the pH of the medium of the two precursors is more basic or more acidic than that of the skin surface, it is then preferable to buffer this medium with a suitable buffer solution in order to bring the pH of this medium back to a value close to 5.5. In practice, the medium containing the two precursors will generally have a pH (typically ranging from 3.5 to 7.5) which is compatible with the activities of the bioconversion enzymes involved.

The first and second precursors used in the present invention are known in the art or can be easily prepared by synthetic methods well-known in the art.

The first precursor is chosen from amide derivatives of an active agent and monosaccharide derivatives of the active agent, which can be hydrolyzed by proteases or peptidases and glycosidases, respectively, as enzymes.

The active agent monosaccharide derivatives are preferably $C_3$ to $C_6$ monosaccharide derivatives. They are chosen, in particular, from glucosyl, mannosyl, fructosyl, fucosyl, N-acetylglucosamine, galactosyl and N-acetylgalactosamine derivatives, N-acetylmuramic acid derivatives, sialic acid derivatives and mixtures thereof.

The amide derivatives of the active agent include, but are not limited to, peptides containing one or more peptide bonds (amide bonds) such as dipeptides, tripeptides, tetrapeptides, etc., preferably containing the naturally occurring amino acids and amide derivatives of peptides, for example, lipotyrosine and trityrosine.

The second active agent precursors may be derivatives which are hydrolyzed by other enzymes, for example, by esterases, phosphatases, sulphatases, and the like. For example, the second active agent precursors may be phosphates; sulphates; active agent palmitates, acetates, propionates, ferulates and, generally speaking, alkyl or acyl esters; and acylated or alkylated ethers. The acyl and alkyl radicals have, in particular, from 1 to 30 carbon atoms.

Preferably, the second precursor is an ester resulting from the reaction of the active agent with an inorganic acid, such as a sulphate or a phosphate to yield a precursor which will react with a sulphatase or phosphatase in contact with the skin, and the second precursor is an acyl or alkyl ester resulting from reaction of the active agent with an organic acid such as palmitic, acetic, propionic, nicotinic, 1,2,3-propanetricarboxylic or ferulic acid to yield a precursor which will react with a specific esterase of the skin.

When several precursors are used as second precursors, they must be chosen in such a way that the enzymatic reactions involved do not inhibit one another. Thus, an active agent tartrate cannot be used in the presence of a phosphate of this active agent, since tartrate is generally an inhibitor of the phosphatase which will hydrolyze the phosphate.

Thus, as an example in the case of vitamins, it is possible to use a first precursor chosen from monosaccharide derivatives of a vitamin and a second precursor chosen from the phosphate, sulphate, palmitate, acetate, nicotinate or propionate of this vitamin. These vitamins are, especially preferably, vitamin A, vitamin C and vitamin E.

Moreover, as an example in the case of lactic acid (α-hydroxy acid), it is possible to use as a first precursor a lactic acid monosaccharide derivative, as a second precursor ethyl lactate and as a third precursor the sulphated derivative of lactic acid (lactic acid sulphate).

As a further example, it is possible to use the glucosyl derivative of quercetin as a first precursor and a quercetin ester such as quercetin ferulate as a second precursor, in order to liberate quercetin synergistically on application to the skin of a composition containing this pair of precursors.

As an ascorbic acid phosphate, it is possible to use the ascorbyl phosphate of an alkali metal, alkaline-earth metal or transition metal, such as magnesium, sodium, potassium, calcium or zinc. As a retinol phosphate, it is possible to use the retinyl phosphate of an alkali metal or alkaline-earth metal, such as magnesium or potassium.

As an organic acid ester of vitamin C, it is possible to use a palmitic, acetic or propionic ester branched at the 2-position or 3-position of vitamin C. As a tocopherol ester, tocopherol nicotinates or acetates may be used. Among retinol esters, a palmitic, propionic or acetic acid ester may be used.

Among vitamin C monosaccharide derivatives which are usable in the invention as a first precursor, there may be mentioned for example, glucosylated, mannosylated, fructosylated, N-acetylglucosaminated and N-acetylmuramic acid derivatives of vitamin C, as well as the fucosylated, galactosylated and N-acetylgalactosaminated derivatives, and the sialic acid derivatives of vitamin C or mixtures thereof.

To obtain a synergy of release of the same active agent from the two precursors, it is preferable to introduce an amount from 1 to 40 millimoles of each precursor, and preferably from 5 to 20 millimoles, the amount by weight to be introduced depending on the molecular weight of the derivatives.

In practice, the first and second precursors are advantageously each present in proportions ranging from 0.1 to 10% by weight, and preferably of about 1.5% by weight, relative to the total weight of the composition. The relative proportion between the first and the second precursor can range from 10:90 to 90:10, and is preferably about 50:50 in terms of molar concentration.

The composition, according to the invention, can take the form of an aqueous or aqueous-alcoholic lotion, an aqueous or anhydrous gel, a serum or an oil-in-water (O/W) or water-in-oil (W/O) emulsion. It can also take the form of spherules, such as liposomes, nanocapsules or nanospheres. These compositions can be prepared using known methods.

When the composition is an emulsion, the proportion of the fatty phase generally ranges from about 5% to 80% by weight, preferably from about 5% to 50% by weight, relative to the total weight of the composition. The oils, emulsifiers and co-emulsifiers used in the composition in emulsion form may be chosen from those which are well-known and traditionally used in cosmetics. The emulsifier and co-emulsifier are present in the composition in a proportion ranging from about 0.3% to 30% by weight, preferably from about 0.5% to 30% by weight, relative to the total weight of the composition.

The composition, according to the invention, may also contain cosmetically and/or dermatologically acceptable additives in amounts which do not interfere with the desired enzymatic reactions. These additives are preferably chosen from surfactants, fats (natural, silicone or synthetic oil), hydrating agents (polyols), preservatives, perfumes, gelling agents (xanthan gum, bentone, carbomer), pigments ($TiO_2$), fillers (talc) and also free vitamins and UV screening agents.

All the constituents which are usable in the invention must, of course, be compatible with the enzymatic reactions involved.

Also within the scope of the invention is also a preferred stabilized composition capable of releasing vitamin C in contact with the skin, characterized in that it contains at least one first vitamin C precursor and at least one second vitamin C precursor, capable of simultaneously releasing this vitamin according to a first specific enzymatic reaction and a second, different specific enzymatic reaction, respectively, and at a faster rate than the sum of the rates of the first enzymatic reaction and of the second enzymatic reaction taken separately, and in that the first precursor is a monosaccharide derivative.

In another preferred embodiment of the composition of the invention, a pair of vitamin C precursors and simultaneously free vitamin E or one of its derivatives are used.

This composition makes it possible to obtain all the cosmetic or dermatological treatment properties of free vitamin C with the same efficacy as the free vitamin with, in addition, an increase in the antioxidant activity of vitamin E relative to its use alone.

The composition according to the invention consists especially of a cosmetic and/or dermatological composition for the cosmetic and/or dermatological treatment of the skin. This composition makes it possible to combat, for example, skin aging, free radicals or skin blotches, dry skin, acne and/or certain skin diseases (dermatitis, psoriasis). This composition may also be used to promote collagen synthesis or promote soothing following an activation of certain skin enzymes induced by stresses (oxidative or pollution-induced), as well as for the cicatrization of wounds.

The scope of the invention also includes the use of the above composition for cosmetic treatment of the skin or for the preparation of a cream intended for a dermatological treatment.

The invention will now be described in greater detail, by way of illustration without implied limitation, by reference to the single attached figure showing the value of using a pair of precursors of the same vitamin, and by means of examples.

EXAMPLES

In a liquid medium buffered to pH 4 with an acetate buffer, there were incorporated magnesium ascorbyl phosphate, glucosylated ascorbyl and different samples of *Stratum corneum* in powder form. The whole composition was mixed and then allowed to stand to react, and the supernatant was then withdrawn. The curves shown in FIG. 1 were obtained by assaying the supernatant using high performance liquid chromatography (HPLC).

Curve 1 was obtained with a zero concentration of magnesium ascorbyl phosphate and a 40 millimolar concentration of glucosylated ascorbyl.

Curve 2 was obtained with a 40 millimolar concentration of magnesium ascorbyl phosphate and a zero concentration of glucosylated ascorbyl.

Curve 3 was obtained with a 20 millimolar concentration of magnesium ascorbyl phosphate and a 20 millimolar concentration of glucosylated ascorbyl.

From FIG. 1, it is clear that there is a marked improvement in the release of ascorbic acid in the free state within the *Stratum corneum* after application to the skin of the composition according to the invention (curve 3) and, more especially, with the high concentrations of substrates.

Examples of compositions according to the invention are given below. The amounts are given therein as weight percentages.

Example 1

W/O emulsion

| Fatty Phase: | |
|---|---|
| Natural oil (shea butter) | 20 |
| Cyclomethicone | 5 |
| Glyceryl monostearate (emulsifier) | 6 |
| Liquid paraffin | 7 |
| Aqueous phase: | |
| Magnesium ascorbyl phosphate | 1.5 |
| Glucosylated ascorbyl | 1.5 |
| Polyol | 3 |
| Xanthan gum | 0.05 |
| Magnesium sulphate | 0.4 |
| Preservatives and perfumes | 1 |
| Water up to | 100 |

The emulsion takes the form of a white cream intended for the treatment of wrinkles and/or small lines due to aging.

Example 2

This example differs from that of Example 1 by the use, in addition, of 0.5 of tocopherol. The cream obtained displays improved antioxidant properties compared to those of Example 1.

Example 3

O/W emulsion

| Octyl Palmitate | 20 |
|---|---|
| PEG-40 stearate (emulsifier) | 2 |
| Cetyl alcohol | 4 |
| Polyol | 5 |
| Cyclomethicone | 5 |
| Phosphated vitamin C | 1 |
| Glucosylated vitamin C | 1 |
| Preservative | 0.2 |
| $TiO_2$ (titanium oxide) | 1 |
| Perfume | 0.5 |
| Carbomer (polyacrylic acid) | 0.15 |
| Water up to | 100 |

The white cream obtained is intended for daily protection of the face.

Obviously, numerous modifications and variations of the present invention are possible in light of the above teachings. It is, therefore, to be understood that within the scope of the appended claims, the invention may be practiced otherwise than as specifically described herein.

What is claimed as new and desired to be secured by Letters Patent of the United States is:

1. A stabilized composition capable of releasing an skin active agent in contact with the skin, comprising:

a first precursor for a skin active agent and a second precursor for said active agent, wherein said first and second precursors simultaneously release said active agent by the action of a first specific enzymatic reaction on said first precursor and by a second specific enzymatic reaction different from said first specific enzymatic reaction on said second precursor, wherein said first precursor comprises a monosaccharide derivative of said skin active agent or an amide derivative of said skin active agent, and wherein the action of said first and second specific enzymatic reactions releases said active agent at a faster rate than the sum of the individual rates of the first enzymatic reaction and the second enzymatic reaction.

2. The composition of claim 1, wherein said composition is obtained by mixing a first solution containing said first precursor and a second solution containing said second precursor to form a mixture, said mixture having a pH of 3.5–7.5.

3. The composition of claim 1, wherein said first and second precursors are selected from the group consisting of vitamins, lipopeptides, lipoamino acids, α- and β-hydroxy acids, antioxidants and hydrating agents.

4. The composition of claim 1, wherein said monosaccharide active agent is selected from the group consisting of glucosyl, mannosyl, fructosyl, fucosyl, N-acetylglucosaminyl, galactosyl, N-acetylgalactosaminyl, N-acetylmuramyl, and sialyl active agents and mixtures thereof.

5. The composition of claim 1, wherein said second precursor is an ester.

6. The composition of claim 1, wherein said second precursor is an active agent acyl ester or alkyl ester.

7. The composition of claim 1, wherein said second precursor is an inorganic acid ester or an organic acid ester.

8. The composition of claim 1, wherein said first precursor is an active agent monosaccharide, and said second precursor is selected from the group consisting of a palmitate, an acetate, a propionate, a nicotinate, a sulphate, a phosphate, a glyceride and a ferulate of said active agent.

9. The composition of claim 8, wherein said first precursor is a $C_3$ to $C_6$ vitamin or quercetin monosaccharide, and said second precursor is selected from the group consisting of ascorbic acid phosphates, retinol phosphates, tocopherol nicotinates, retinol palmitates, ascorbic acid palmitates, tocopherol acetates, retinol acetates, ascorbic acid acetates, retinol propionates, ascorbic acid propionates, quercetin palmitates, quercetin acetates, quercetin propionates, quercetin ferulates, and mixtures thereof.

10. The composition of claim 9, wherein said first precursor is a $C_3$ to $C_6$ vitamin monosaccharide and said vitamin monosaccharide is selected from the group consisting of glucosyl, mannosyl, fructosyl, fucosyl, N-acetylglucosaminyl, galactosyl, N-acetylgalactosaminyl, N-acetylmuramyl, and sialyl vitamin monosaccharides and mixtures thereof.

11. The composition of claim 1, wherein said first active agent precursor and said second active agent precursor are each, independently, present in a proportion ranging from 0.1 to 10% by weight relative to the total weight of the composition.

12. The composition of claim 11, wherein said first active agent precursor and said second active agent precursor are each present in a molar proportion of 50:50.

13. The composition of claim 1, further comprising an additive selected from the group consisting of perfumes, surfactants, fats, hydrating agents, preservatives, gelling agents, pigments, fillers, UV screening agents and mixtures thereof.

14. The composition of claim 1, comprising a water-in-oil or oil-in-water emulsion.

15. The composition of claim 14, wherein said oil comprises from 5% to 80% by weight relative to the total weight of the composition.

16. The composition of claim 1, comprising a plurality of different first active agent precursors, a plurality of different second active agent precursors or a mixture thereof.

17. A stabilized composition capable of releasing vitamin C in contact with the skin, comprising:

a first vitamin C precursor and a second vitamin C precursor, wherein said first and second vitamin C precursors simultaneously release vitamin C by the action of a first specific enzymatic reaction on said first vitamin C precursor and by a second specific enzymatic reaction different from said first specific enzymatic reaction on said second vitamin C precursor, wherein said first vitamin C precursor is a glucosyl vitamin C and said second vitamin C precursor is a vitamin C phosphate ester, and wherein the action of said first and second specific enzymatic reactions releases vitamin C at a faster rate than the sum of the individual rates of the first enzymatic reaction and the second enzymatic reaction.

18. The composition of claim 17, comprising magnesium ascorbyl phosphate and glucosylated ascorbic acid.

19. The composition of claim 17, further comprising tocopherol or a tocopherol derivative.

20. A method for treating skin aging, skin depigmentation, dry skin or acne, for promoting collagen synthesis, for absorbing skin free radicals, or promoting the soothing of the skin, comprising contacting skin with the composition of claim 1.

21. A method for the cicatrizing dermatological treatment of wounds, comprising contacting a dermatological wound with the composition of claim 1.

22. A composition, comprising:

(a) a first component comprising a monosaccharide or an amide of a skin active agent; and (b) a second component comprising a phosphate, a sulfate, an alkyl ester, an acyl ester, an alkyl ether or an acyl ether of said skin active agent.

23. The composition of claim 22, wherein said skin active agent is selected from the group consisting of vitamin A, vitamin C, vitamin E, lactic acid, quercetin and retinol.

24. The composition of claim 23, wherein said skin active agent is vitamin C.

25. The composition of claim 24, wherein said first component is a glucosylated vitamin C and said second component is a vitamin C phosphate.

26. The composition of claim 22, wherein said second component is selected from the group consisting of a palmitate, an acetate, a propionate, a nicotinate, a sulfate, a phosphate, a ferrulate and a 1,2,3-propanetricarboxylate of said skin active agent.

27. The composition of claim 22, comprising said first component and said second component in an amount ranging from 0.1 to 10% by weight relative to the total weight of said composition wherein the relative proportion between said first component and said second component is in the range from 10:90 to 90:10.

28. The composition of claim 24, comprising said first component and said second component in an amount ranging from 0.1 to 10% by weight relative to the total weight of said composition wherein the relative proportion between said first component and said second component is in the range from 10:90 to 90:10.

* * * * *

UNITED STATES PATENT AND TRADEMARK OFFICE
CERTIFICATE OF CORRECTION

PATENT NO. : 5,607,921
DATED : MARCH 4, 1997
INVENTOR(S) : DOMINIQUE BERNARD, ET AL.

It is certified that error appears in the above-identified patent and that said Letters Patent is hereby corrected as shown below:

Column 7, line 8, "an skin" should read --a skin--.

Signed and Sealed this

Thirtieth Day of June, 1998

Attest:

BRUCE LEHMAN

*Attesting Officer*  *Commissioner of Patents and Trademarks*